US00PP17747P3

(12) United States Plant Patent
Drewlow

(10) Patent No.: US PP17,747 P3
(45) Date of Patent: May 22, 2007

(54) **NEW GUINEA *IMPATIENS* PLANT NAMED 'APPLAUSE ORANGE BICOLOR'**

(50) Latin Name: *Impatiens hawkeri*
Varietal Denomination: Applause Orange Bicolor

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 115 days.

(21) Appl. No.: 11/177,717

(22) Filed: Jul. 8, 2005

(65) Prior Publication Data

US 2007/0011791 P1 Jan. 11, 2007

(51) Int. Cl.
*A01H 5/00* (2006.01)

(52) U.S. Cl. ..... Plt./318

(58) Field of Classification Search ..... Plt./318
See application file for complete search history.

*Primary Examiner*—Kent Bell
*Assistant Examiner*—Louanne Krawczewicz Myers
(74) *Attorney, Agent, or Firm*—The Webb Law Firm

(57) ABSTRACT

'Applause Orange Bicolor' is a new variety of New Guinea *Impatiens* that exhibits compact growth and large orange and white colored flowers.

1 Drawing Sheet

Botanical classification: *Impatiens hawkeri.*
Varietal denomination: 'Applause Orange Bicolor'.

BACKGROUND OF THE INVENTION

The present invention comprises a new and distinct cultivar of *Impatiens hawkeri* known by the varietal name 'Applause Orange Bicolor'. The new variety was discovered in Lompoc, Calif. The new variety is a result of cross breeding Seedling #95-209-1 (female parent) (unpatented) and Seedling #96-1181-2 (male parent) (unpatented). The purpose of the breeding program was to develop a cultivar that achieved early flowering 6 to 8 weeks from rooted cuttings and to achieve at least a 4 cm flower. Further, the purpose was to develop a cultivar with a compact, mounded growth habit that flowered above the leaf canopy. Comparisons between the new variety and its parents cannot be made, as the parental varieties no longer exist. The new variety is similar in growth habit and vigor to 'Kiziz' (U.S. Plant Pat. No. 11,931), but is mounded in shape, instead of upright. The new variety was first asexually reproduced by stem tip cuttings in Lompoc, Calif. The new variety has been trial and field tested and has been found to retain its distinctive characteristics and remain stable and true to type through successive propagations of asexual reproductions. Characteristics that distinguish the new variety from others known to the breeder include:

- Compact, self branching, early flowering nature of cultivar makes it ideal for 10 cm pots and small 20 cm baskets;
- Ideal for mass production growers as the new variety can be grown at a very tight spacing;
- Can be grown in areas with high night temperatures where taller growing cultivars overgrow their containers;
- Large (up to 70 mm in diameter) orange and white flowers;
- Large overlap of petals that are carried over the leaf canopy;

- Cultivar can be finished in 7 weeks from a rooted cutting, making it ideal for fast cropping;
- Mounded, compact growth habit makes cultivar ideal for border plantings and small spaces;
- Able to tolerate both high temperature and full sun conditions as demonstrated by trials in Connellsville, Pa. during the summer,
- Able to tolerate cool night temperatures (5–10° C.) as demonstrated in outdoor trials in Lompoc, Calif. and
- Resistant or tolerant to disease and insect problems.

The new variety was grown in a 15 cm container in Lompoc, Calif. under Dynaglass with 30% shade and 21–24° C. day temperatures and 16–18° C. night temperatures. The new variety initiates roots in 10 days in the summer and 12 days in the winter at 21° C. The new variety exhibits developed roots at 21 days at an average temperature of 21° C. Its rooting habit is very dense, fibrous and freely branching with fine roots on young plants and ropey roots on mature plants.

DESCRIPTION OF THE DRAWING

The accompanying photographic drawing illustrates the new variety, with the color being as nearly true as is possible with color illustrations of this type.

DESCRIPTION OF THE PLANT

Figure 1:
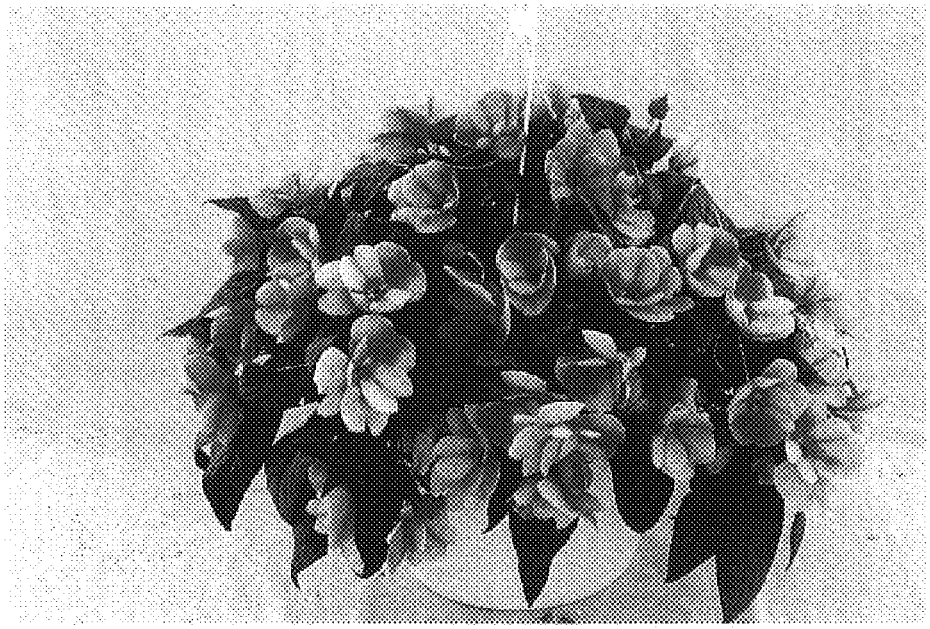

The following detailed description sets forth the characteristics of the new cultivar. The data which defines these characteristics were collected by asexual reproductions carried out in Lompoc, Calif. The color readings were taken indoors under 3500–4000 foot candles of light. The new variety was fourteen weeks old when described. Color references are primarily to the 1966 R.H.S. Colour Chart of The Royal Horticultural Society of London.

PLANT

Form: Mounded.
Height (from soil to top of flowers): 12 to 15 cm.

Plant diameter: 30 to 35 cm.
Vigor: Vigorous.
Branching habit: Highly self-branched.
Lateral branches:
*Color.*—146C.
*Texture.*—Fine hairs; pubescent.
*Length.*—12 to 15 cm, varies with location.
*Diameter.*—5 to 6 mm and variable.
*Internode length.*—3 to 4 cm and highly variable.
*Strength.*—Strong.
*Quantity.*—10 or more, depending on the age of the plant.
Foliage:
*Arrangement.*—In a whorl of 5 or 6 leaves.
*Number of leaves per stem.*—20 or more.
*Size of leaf.*—Length: 10 to 11 cm. Width: 3 to 3.5 cm.
*Shape of leaf* (*generally*).—Lanceolate.
*Shape of apex.*—Acuminate.
*Shape of base.*—Acute.
*Texture.*—Glabrous.
*Aspect.*—Upward facing — angle varies from 45 to 60° to stem.
*Margin type.*—Finely serrated with fine ciliate.
*Fragrance.*—None.
*Color.*—Young leaves: Upper surface: 147A with very heavy 200A cast. Lower surface: 187C. Mature leaves: Upper surface: 147A with 185A cast. Lower surface: 185A.
*Petiole.*—Length: 8 to 10 mm. Diameter: 4 mm. Color: 185C. Texture: Glabrous.
*Veins.*—Venation pattern: Pinnate. Color: Upper surface: 185C. Lower surface: 185A.

FLOWER

Natural flowering season at specified locations: Year-round and not affected by a day length under greenhouse conditions.
Flower type and habit: Hypogynous — flowers over leaf canopy. Petals self-cleaning; gynoecium persistent.
Number of flowers per plant: 30 flowers at 14 weeks. The number increases as plants get older.
Time of day of flower opening: Morning.
Fragrance: None.
Longevity: 5 or more days depending upon environment.
Flower height: Flat.
Flower diameter: 70 mm.
Bud:
*Stage of development when described.*—Just before opening.
*Shape.*—Ellipsoidal.
*Diameter.*—12 mm.
*Length.*—20 mm.
*Color.*—44A with small area of 33A.
Petals:
*Arrangement.*—Whorl with petals overlapping and round.
*Quantity.*—5.
*Length.*—Banner petal: 35 mm. Lateral: 35 mm. Base: 40 mm.
*Width.*—Banner petal: 45 mm. Lateral: 30 mm. Base: 40 mm.
*Shape.*—Heart.
*Apex.*—Round with 5 to 10 mm indentation.
*Base.*—Rounded to acute.
*Margin.*—Entire.
*Texture.*—Smooth and glabrous.
*Color.*—When opening: Banner petal and base petals: Upper surface: 51A eye area, 41A midrib, with the balance being 43D. Lower surface: 41B to 41C at edges. Lateral petals: Upper surface: 51A eye area, 41A midrib, with the balance being 55 D. Lower surface: 41B to 41C at edges. Fully opened: Banner petals: Upper surface: 51A eye area, 40B around midrib, and 50D at the edge. Lower surface: 41C to 50D. Lateral and base petals (upper and lower surfaces): Same as above.
Spur:
*Quantity.*—1.
*Length.*—2 mm.
*Diameter at apex.*—1 mm.
*Diameter at flower.*—70 mm.
*Aspect.*—At base, parallel to peduncle, then bending to a 90° angle.
*Color.*—146D with a 146A tip.
Peduncles:
*Length.*—6 cm.
*Diameter.*—2 mm.
*Color.*—146C.
*Texture.*—Glabrous.
*Orientation.*—45° angle from stem.
*Strength.*—Strong.
Disease/pest resistance: No susceptibility has been noted to date.
Weather tolerance: Resistant to rain but not strong winds.
Lasting quality:
*On plant.*—5 or more days.
*Of cut flowers.*—Not applicable.
Seed production and description: Not applicable.
Fruit production and description: Not applicable.

REPRODUCTIVE ORGANS

Stamens:
*Number* (*per flower*).—5.
*Filament length.*—Not applicable.
*Anthers.*—Shape: Hooded. Length: 6 mm. Color: 155C base color with 68B cast on hood.
*Pollen.*—Color: 155C. Amount: Abundant.
Pistils:
*Length.*—7 mm.
*Styles.*—Length: Less than 1 mm. Color: Off-white with 184C cast.
*Stigma.*—Shape: 5 segmented column. Color: Off-white with 184C cast. Ovary color: 184A.

I claim:

1. A new and distinct variety of New Guinea *Impatiens* plant, named 'Applause Orange Bicolor', as described and illustrated.

* * * * *